United States Patent [19]  
Wu

[11] Patent Number: 4,849,549  
[45] Date of Patent: Jul. 18, 1989

[54] PROCESS FOR PREPARATION OF RESORCINOL

[75] Inventor: Ching-Yong Wu, Pittsburgh, Pa.

[73] Assignee: Indspec Chemical Corporation, Pittsburgh, Pa.

[21] Appl. No.: 136,317

[22] Filed: Dec. 22, 1987

[51] Int. Cl.$^4$ ............................................ C07C 37/08
[52] U.S. Cl. .................... 568/768; 568/763; 568/771
[58] Field of Search ............ 568/568, 768, 570, 771, 568/571, 563

[56] References Cited

U.S. PATENT DOCUMENTS

| | | | |
|---|---|---|---|
| 3,911,030 | 10/1975 | Suda et al. | 568/753 |
| 3,923,908 | 12/1975 | Suda et al. | 568/768 |
| 3,928,469 | 12/1975 | Suda et al. | 568/753 |
| 3,929,920 | 10/1975 | Suda et al. | 568/753 |
| 3,932,528 | 1/1976 | Suda et al. | 568/568 |
| 3,950,431 | 4/1976 | Suda et al. | 568/568 |
| 3,953,521 | 4/1976 | Suda et al. | 568/568 |
| 3,969,420 | 7/1976 | Suda et al. | 568/753 |
| 4,229,596 | 10/1980 | Burkholder et al. | 568/768 |
| 4,237,319 | 12/1980 | Nambu et al. | 568/568 |
| 4,239,921 | 12/1980 | Hashimoto et al. | 568/753 |
| 4,267,387 | 5/1981 | Imai et al. | 568/568 |
| 4,273,623 | 6/1981 | Hashimoto et al. | 568/753 |
| 4,283,570 | 8/1981 | Nakagawa et al. | 568/769 |
| 4,339,615 | 7/1982 | Imai et al. | 568/768 |
| 4,463,199 | 7/1984 | Chiyoda et al. | 568/768 |
| 4,670,609 | 6/1987 | Bennett et al. | 568/768 |

FOREIGN PATENT DOCUMENTS

| | | | |
|---|---|---|---|
| 1056407 | of 1979 | Canada. | |
| 1115733 | 1/1982 | Canada | 568/768 |
| 0105019 | 4/1984 | European Pat. Off. | 568/768 |
| 2737302 | 2/1978 | Fed. Rep. of Germany | 568/768 |
| 7853626 | 5/1978 | Japan | 568/753 |
| 921557 | 3/1963 | United Kingdom | 568/768 |
| 2061926 | 5/1981 | United Kingdom | 568/753 |
| 2071662 | 9/1981 | United Kingdom | 568/768 |

OTHER PUBLICATIONS

U.S. Ser. No. 136,313, filed 12/22/87.  
U.S. Ser. No. 136,315, filed 12/22/87.

Primary Examiner—Werren B. Lone  
Attorney, Agent, or Firm—Kirkpatrick & Lockhart

[57] ABSTRACT

A process for the preparation of resorcinol from diisopropylbenzene includes the steps of oxidizing m-diisopropylbenzene under anhydrous, non-alkaline conditions with oxygen, extracting m-diisopropylbenzene dihydroperoxide and m-diisopropylbenzene hydroxyhydroperoxide with dilute sodium hydroxide, reextracting with an organic solvent, converting m-diisopropylbenzene hydroxyhydroperoxide to m-diisopropylbenzene dihydroperoxide with hydrogen peroxide, drying the product, decomposing the m-diisopropylbenzene dihydroperoxide in the presence of a catalyst selected from the group consisting of boron trifluoride, ferric chloride and stannic chloride to coproduce resorcinol and actone, and purifying the resorcinol.

15 Claims, 1 Drawing Sheet

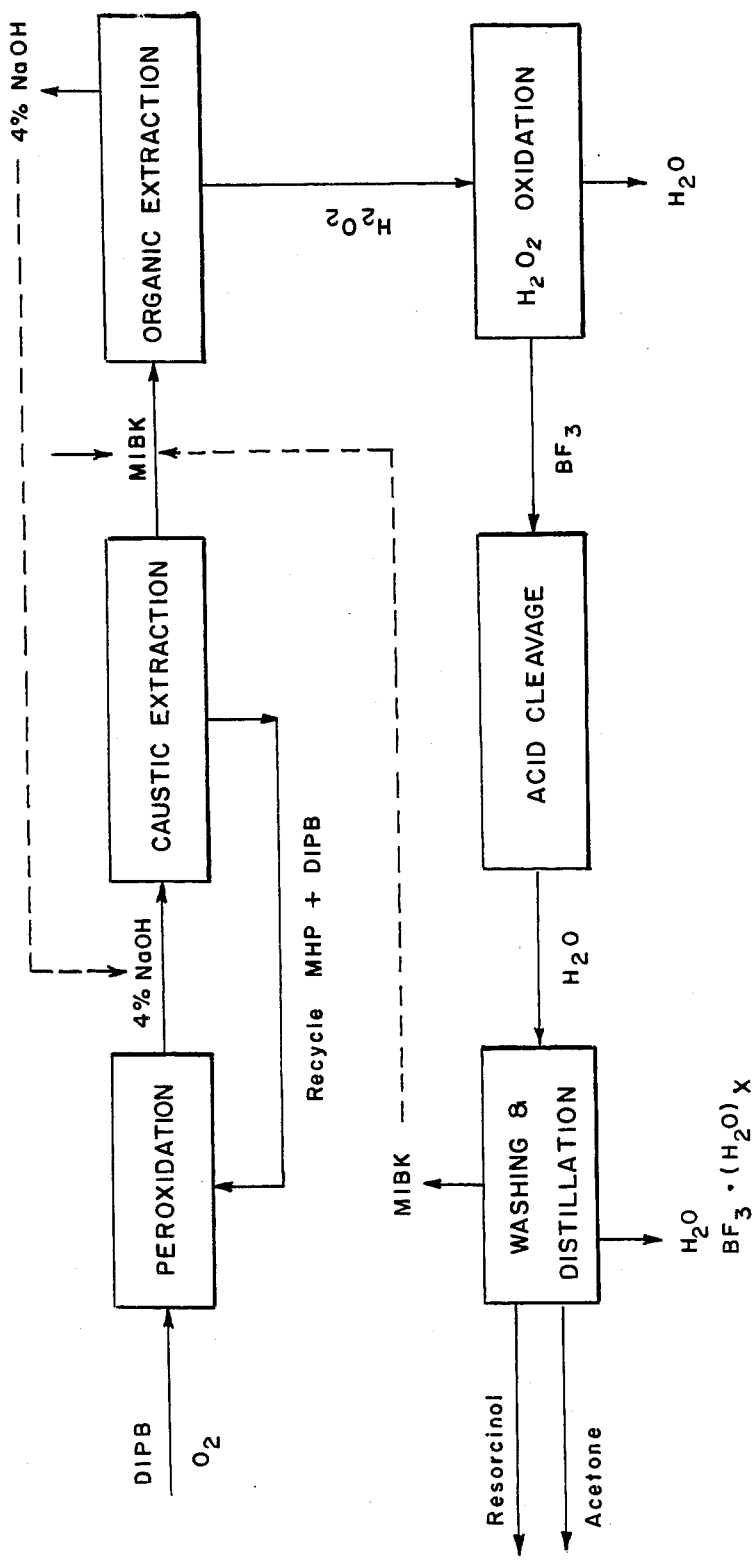

PROCESS FOR PREPARATION OF RESORCINOL

BACKGROUND OF THE INVENTION

1. Field of the Invention

The present invention relates to processes for the preparation of resorcinol, and more particularly to the preparation of resorcinol by hydroperoxidation of diisopropylbenzene.

2. Description of the Prior Art

Resorcinol, or 1,3-benzenediol, has numerous industrial applications, such as its use in the manufacture of fluorescein, eosin, and other dyes, synthetic drugs, and photographic developers or its use as a reagent, reducing agent, external dehydrant, antiseptic, antiferment and bactericide. A well known method of preparing resorcinol has been via a sulfonation-fusion process. Another known method is via the cyclization of methyl 4-oxocaproate from methyl acrylate and acetone followed by dehydrogenation.

In 1972, researchers at the Stanford Research Institute reviewed a new route for the preparation of resorcinol via hydroperoxidation. The Stanford process involves production of a m-diisopropylbenzene (m-DIPB) by alkylation of benzene and/or cumene with propylene, followed by oxidation of the m-DIPB to the diisopropylbenzene dihydroperoxide (DHP). The DHP is decomposed with the aid of an acid catalyst to form resorcinol and acetone.

Numerous patents have since issued which pertain to the preparation of resorcinol by hydroperoxidation.

One commercial process, believed to be practiced by the Sumitomo Chemical Company, Ltd. is described in part by Suda et al. U.S. Pat. No. 3,953,521, British Patent Specification No. 921,557, Suda et al. U.S. Pat. No. 3,950,431, Suda et al. U.S. Pat. No. 3,923,908, Suda et al. U.S. Pat. No. 3,928,469, and Japanese Pat. No. 61-327 and Japanese Kokai No. 58-88357. The Sumitomo process involves the continuous production of m- and p-DHP by hydroperoxidation of m- and p-DIPB in liquid phase using an alkali catalyst, such as 10–20 vol % of a 2% sodium hydroxide (NaOH) solution at 95°–115° C. and air at a pressure within the range of atmospheric to 10 atmospheres. The hydroperoxidation product is extracted with a 4% aqueous sodium hydroxide solution to separate DHP and m-diisopropylbenzene hydroxyhydroperoxide (HHP) from unreacted m-DIPB and diisopropylbenzene monohydroperoxide (MHP). The MHP/m-DIPB fraction is recycled to the hydroperoxidation reaction vessel. The DHP/HHP fraction, in the form of an aqueous solution containing sodium salts of DHP and HHP, is heated to 80° C. and extracted with methyl isobutyl ketone (MIBK) to recover DHP and HHP. The MIBK solution of DHP/HHP is then washed with an organic solvent to reduce the HHP content, and mixed with an acid catalyst, such as 0.5-2% concentrated sulfuric acid ($H_2SO_4$) and, in some instances, hydrogen peroxide ($H_2O_2$) to decompose the DHP to either resorcinol or hydroquinone and acetone. The decomposition product is then neutralized with an aqueous ammonia solution, then distilled to obtain crude resorcinol or hydroquinone. Methods for purifying the crude resorcinol are described in Suda et al. U.S. Pat. Nos. 3,929,920; 3,911,030, and 3,969,420, and Japan Kokai No. 78-53626 and British Pat. No. 2,061,926 A.

Another commercial process, believed to be practiced by Mitsui Petrochemical Industries, is described in Nambu et al. U.S. Pat. No. 4,237,319, Imai et al. U.S. Pat. No. 4,267,387, Nakagawa et al. U.S. Pat. No. 4,283,570, Imai et al. U.S. Pat. No. 4,339,615, and Japan Kokai Nos. 61-180764 and 59-212440. The Mitsui process involves the hydroperoxidation of m-DIPB with molecular oxygen under aqueous alkaline conditions, for example, in the presence of 2% sodium hydroxide at 80° C.–110° C. for a period sufficient to react at least 90% of the DIPB. The hydroperoxidation product is dissolved in toluene and the aqueous sodium hydroxide solution is recycled to the hydroperoxidation reaction vessel for further use. The toluene solution is treated with excess hydrogen peroxide in the presence of small amounts of sulfuric acid to convert HHP and m-diisopropylbenzene dicarbinol (DCL) to DHP. The by-product water is azeotropically continuously removed. The toluene solution of DHP is then decomposed to resorcinol and acetone with concentrated sulfuric acid in substantial absence of hydrogen peroxide. The decomposition product is washed with aqueous sodium sulfate ($Na_2SO_4$) and distilled to obtain crude resorcinol.

A process for recovery of the resorcinol from the acetone/resorcinol, mixture is described in Hashimoto et al. U.S. Pat. No. 4,273,623. The acid-decomposition reaction mixture is subjected to distillation to separate the resorcin containing concentrate from the acetone, wherein water is added to the decomposition reaction mixture in 20–70% by weight based on the weight of the resorcinol prior to distillation. Additional methods of purifying the crude resorcinol are described in Hashimoto et al. U.S. Pat. No. 4,239,921 and Canadian Pat. No. 1,115,733.

The commercial processes described above each include a peroxidation step employing oxygen or air and aqueous sodium hydroxide for converting DIPB to DHP and other by-products, an extraction step for separating DHP from the peroxidation by-products, an acid cleavage step employing sulfuric acid for decomposing DHP to either resorcinol or hydroquinone and acetone, a neutralization step and a distillation step to purify the crude resorcinol or hydroquinone.

The extraction step in the Sumitomo process includes a caustic extraction with 4% sodium hydroxide followed by organic extraction with MIBK. The Sumitomo process employs hydrogen peroxide in addition to the sulfuric acid in the acid cleavage step. The extraction step in the Mitsui process involves only organic extraction with toluene and is followed by oxidation with hydrogen peroxide and removal of water.

It is believed that neutralization in the Sumitomo process is by means of aqueous ammonia and removal of aqueous ammonium hydrogen sulfate (($NH_4$)$HSO_4$). It is also believed that neutralization in the Mitsui process is by means of aqueous sodium sulfate and subsequent removal of aqueous sodium hydrogen sulfate ($NaHSO_4$). The organic solvents in each process, MIBK and toluene, respectively, are removed in the distillation step and recycled for use in the organic extraction step.

The hydroperoxidation of DIPB produces a variety of by-products in addition to the desired DHP. Isolation of DHP from the oxidation products without causing its decomposition has been the object of several patent disclosures. British Patent Application GB NO. 2 071 662 A discloses the use of superacids such as boron trifluoride in the preparation of resorcinol from m-DIPB. British Pat. No. 921,557, referenced above, disclosed the principle that DHP can be extracted from aqueous alkaline solutions in a much more favorable manner at higher temperatures (e.g. 80° C.) than ambient temperature. The direct extraction method, however, has a very serious problem; that is, the decomposition of DHP to HHP (and to a lesser degree to DCL) during the alkaline extraction process. Sumitomo Chemical Company, Ltd. owns several patents dealing with a method for extracting DHP. One Sumitomo process described in Canadian Pat. No. 1,056,407, discloses extracting DHP by a counter current multistage extraction with a temperature gradient between each stage and with all of the extractions being made at a temperature from 0° to 85° C. and the aqueous alkali solution being fed to the lower temperature zone. Another Sumitomo patent, U.S. Pat. No. 3,932,528, disclosed that in order to prevent the DHP loss during the alkaline extraction, 0.01 to 1 wt % of ammonia or aromatic amine (based on the weight of the solution) is added to the aqueous alkaline solution.

An object of the present invention is to improve the yield of resorcinol in a commercial process. A further object of the invention is to improve the selectivity to DHP in the hydroperoxidation step.

SUMMARY OF THE INVENTION

The objects of the present invention are satisfied by a new process for the preparation of resorcinol by the hydroperoxidation route. Generally, the process of the present invention proceeds as follows. An m-DIPB rich feed stream is hydroperoxidized using a new anhydrous, non-alkaline process. The hydroperoxidation product is extracted with dilute sodium hydroxide to separate m-DHP and m-HHP from unreacted m-DIPB and the other hydroperoxidation products. The m-DHP/m-HHP product is re-extracted from the sodium hydroxide solution with an organic solvent, preferably MIBK, and preferably then oxidized with a hydrogen peroxide solution to obtain pure m-DHP. The m-DHP is then decomposed in the presence of a minute quantity of a catalyst selected from the group consisting of a boron trifluoride and stannic chloride, to coproduce resorcinol and acetone. The yield of resorcinol from the DHP/HHP hydroperoxidation product is between 85 and 90%. The overall molar yield of resorcinol is 80 to 86% from m-DIPB.

BRIEF DESCRIPTION OF THE FIGURE

The FIGURE is a schematic illustration of the process of the present invention.

DETAILED DESCRIPTION OF THE PREFERRED EMBODIMENT

In the process of the present invention, shown schematically in the Figure, a feed stream, comprised of major amounts of m-DIPB and less than about 6% o-DIPB is oxidized with oxygen or air in a nonaqueous, non-alkaline system at about 85° C.–95° C. The hydroperoxidation product is extracted with dilute aqueous sodium hydroxide to separate the DHP/HHP fraction as in the Sumitomo process. About 80% of the remaining hydroperoxidation products, including the MHP/unreacted DIPB fraction is recycled to the feed stream for further hydroperoxidation. The aqueous sodium hydroxide solution is extracted back with hot MIBK to recover the DHP/HHP product. The MIBK is evaporated. The DHP/HHP product is then preferably dissolved in toluene and treated with hydrogen peroxide in the presence of a small amount of sulfuric acid to convert most of the HHP to DHP without decomposing DHP. Finally the DHP is decomposed to resorcinol and acetone using a new catalyst, preferably boron trifluoride ($BF_3$)-etherate. The catalyst is very effective and only a minute amount is required. Alternatively, stannic chloride or ferric chloride may be used as the catalyst in the decomposition step. The decomposition product is purified by any suitable means, such as washing with dilute sodium hydroxide and distilling to obtain resorcinol.

There are three unique steps in the hydroperoxidation process of the present invention. They are (1) hydroperoxidation of m-DIPB to m-DHP, (2) oxidation of by-product m-HHP to m-DHP with hydrogen peroxide ($H_2O_2$), and (3) decomposition of m-DHP to resorcinol and acetone.

The remaining steps include: (1) the preparation of m-DIPB by the Friedel-Crafts alkylation of benzene with propylene; (2) extraction of the m-DHP/m-HHP fraction from the hydroperoxidation mixture with dilute sodium hydroxide; and (3) separation and purification of resorcinol by known techniques.

Peroxidation Of m-DIPB

In prior art hydroperoxidation processes, DIPB is oxidized in a pressurized reactor with either air or molecular oxygen in the presence of sufficient dilute aqueous sodium hydroxide to maintain the pH between 7 and 9. In the present invention, the oxidation of DIPB with oxygen is carried out without using dilute aqueous sodium hydroxide.

In the prior art hydroperoxidation processes, m-DIPB is reacted with oxygen in the liquid phase at 80° to 130° C. In commercial scale processes the reaction is run at temperatures in the upper portion of the range, 95° to 100° C. The higher temperatures in turn require higher pressure to prevent evaporation. Here m-DIPB is oxidized first to monohydroperoxide (MHP) which in turn is oxidized to dihydroperoxide (DHP). Since both MHP and DHP are thermally unstable under the peroxidation conditions, at higher temperatures many other products are also formed. In the initial stages of the oxidation, MHP is the main product because the concentration of DIPB is much greater than MHP. While being oxidized to DHP, MHP can also give up one oxygen atom to form a monocarbinol (MCL, isopropylphenyldimethyl carbinol) which in turn can be oxidized to hydroxyhydroperoxide (HHP), as follows:

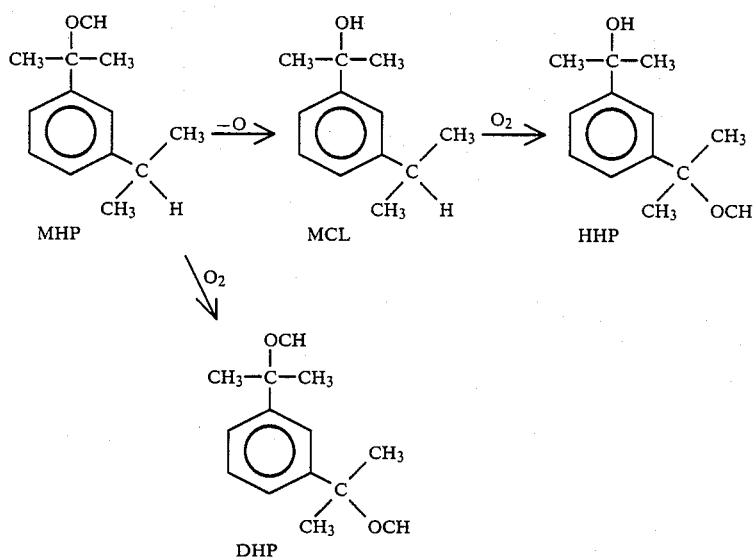

At the same time, smaller amounts of the corresponding monoketone (MKT) and ketone hydroperoxide (KHP) are formed, by splitting off methanol from MHP and DHP, respectively. The KHP can lose another molecule of methanol to form a diketone (DKT, 1,3-diacetylbenzene).

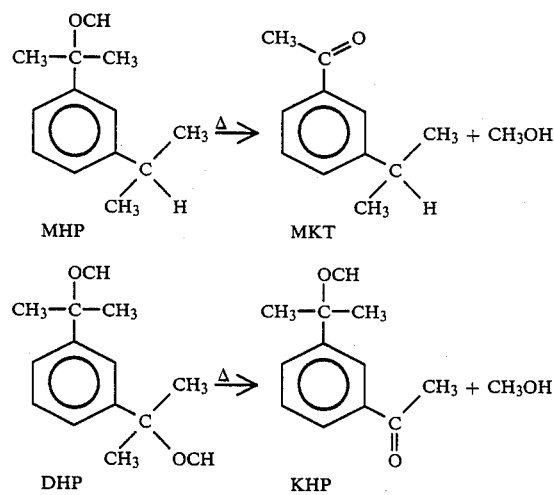

At the temperature employed in the prior art systems for the oxidation of DIPB (80°–130° C.), the ratio of ketone formation to carbinol formation is roughly 1 to 3. Finally, the HHP may lose an oxygen atom to form a dicarbinol (DCL). All the products mentioned above have been found in the oxidation product of m-DIPB. However, the three products present in the largest amount are MCL, DCL and diisopropylbenzene olefin carbinol (OLCL), which are formed by dehydration of DCL.

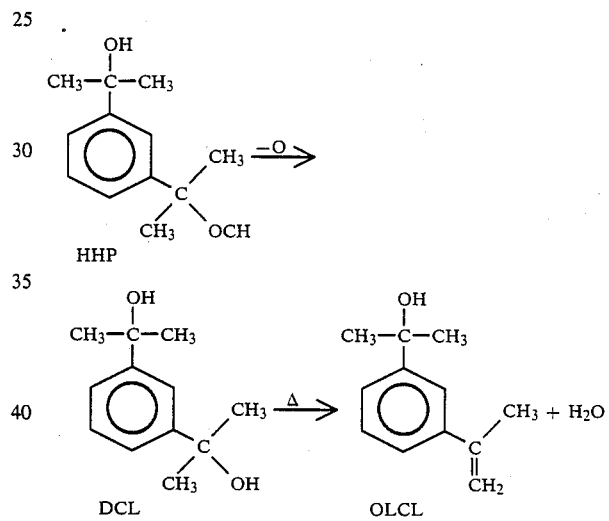

EXAMPLE I

Hydroperoxidation Under Anhydrous, Non-Alkaline Conditions

Table I shows the analysis of products from the hydroperoxidation of CP grade m-DIPB in a nonaqueous, non-alkaline medium.

Hydroperoxidation was made in a one-liter 3-neck flask equipped with a stirrer, thermometer, reflux condenser, and gas-bubbler. The reaction mixture in the flask was stirred and heated to the desired temperature with a heating mantle while approximately 100 ml/min. oxygen was bubbled through the reaction mixture.

In the initial hydroperoxidation, when no recycle m-MHP/m-DIPB was used, 700 g CP grade m-DIPB and 30 g initiator, which was a 51% m-MHP/m-DIPB mixture, were used as the starting material. In the subsequent recycle experiments (Recycle Runs 1 to 9), the recycle m-MHP/m-DIPB fraction (usually about 650 g) was mixed with enough fresh m-DIPB to make 750 g of starting material.

During the hydroperoxidation, a small sample (0.5 g) was removed from the reaction mixture every four hours and titrated iodometrically to determine total peroxide concentraiton expressed as % MHP.

$$\% \, MHP = \frac{[ml \, 0.1 \, N \, Na_2S_2O_3 \, solution] \, [0.1] \, [MWMHP] \times 100}{[Sample \, weight, \, g] \times 2 \times 1000}$$

Hydroperoxidation was terminated when the titrated % MHP value reached about 75%–80%, which normally took about 16 to 24 hours.

The DHP/HHP product was obtained by extracting the hydroperoxidation product with dilute aqueous alkaline solution. The remaining organic phase, which contained about a 2:1 ratio of MHP/DIPB, was recycled. In the cyclic hydroperoxidation, the recycle MHP/DIPB was mixed with fresh DIPB equivalent to the amount of DHP/HHP product removed in order to maintain the same moles of MHP and DIPB throughout the cyclic process. In the actual operation, a constant weight of hydroperoxidation feed was charged in all 9 cycles of hydroperoxidation to meet this requirement.

TABLE I

| | DHP/HHP from CP m-DIPB, 100% Recycle | | | | | | | | | |
|---|---|---|---|---|---|---|---|---|---|---|
| | Conditions | | | DHP/HHP | | MHP/DIPB Recycle | | DIPB | Net Production[2] | | |
| Recycle No. | time hrs | temp. °C. | MHP,[1] % | wt, g | DHP,[1] % | wt, g | MHP,[1] % | Conv.[2,3] % | DHP Mol % | HHP Mol % | DHP/DHP + HHP % |
| 0 | 32 | 82–88 | 73.3 | 161.0 | 89.5 | 674 | 54.9 | 66.3 | 14.8 | 1.7 | 89.7 |
| 1 | 16 | 84–85 | 75.4 | 100.3 | 85.5 | 685 | 59.7 | 43.5 | — | — | — |
| 2 | 16 | 83–85 | 75.9 | 96.5 | 83.6 | 661 | 61.6 | — | 9.0 | 2.7 | 76.9 |
| 3 | 16 | 84–85 | 77.9 | 126.4 | 87.8 | 648 | 62.2 | 41.7 | 12.5 | 2.2 | 85.0 |
| 4 | 24 | 85 | 86.2 | 183.0 | 86.1 | 613 | 56.6 | 53.4 | 17.2 | 2.2 | 88.7 |
| 5 | 24 | 85–86 | 76.5 | 84.3 | 88.2 | 663 | 62.9 | 48.8 | 8.0 | 2.6 | 75.5 |
| 6 | 24 | 85–90 | 77.7 | 128.0 | 84.7 | 651 | 56.1 | 43.6 | 9.9 | 2.7 | 78.6 |
| 7 | 24 | 83–87 | 73.5 | 79.5 | 82.2 | 690 | 61.6 | 40.8 | 7.9 | 2.5 | 76.0 |
| 8 | 24 | 85–91 | 75.7 | 83.8 | 81.0 | 697 | 63.7 | 35.1 | 7.4 | 3.8 | 66.1 |
| 9 | 24 | 87–93 | 71.6 | 77.0 | 73.6 | 708 | 59.4 | 32.6 | 4.6 | 4.2 | 52.2 |
| Av. 1–9 | | | 76.7 | 106.5 | 83.6 | 668 | 60.4 | 42.4 | 8.5 | 2.5 | 77.0 |

[1]By iodometric titration.
[2]Calculated from high performance liquid chromatographic analysis (HPLC).
[3]These conversions were calculated from data obtained under variable caustic extraction conditions.

Columns 3, 5 and 7 of Table I represent results of iodometric titration expressed as wt % MHP, DHP, and MHP, respectively. The iodometric titration determines the amount of active oxygen in the sample which is calculated as though it were a single hydroperoxide. It cannot be used to distinguish different hydroperoxides.

Data shown in columns 8, 9, and 10 of Table I were obtained by high performance liquid chromatographic (HPLC) analysis. They show the net conversion of DIPB and net production of DHP and HHP (as mol %) for each cycle of hydroperoxidation. The last line of Table I shows the average values for cycles 1 to 9.

A quantitative determination of a mixture of hydroperoxides was made by HPLC analysis. Pure samples of DHP, MHP, DCL, OLCL, DKT, MCL, MKT, and HHP were used for the calibration of HPLC data. The results are shown in Table II.

TABLE II

| Composition of Product From Hydroperoxidation of CP m-DIPB | | | | | | | | | |
|---|---|---|---|---|---|---|---|---|---|
| | COMPONENTS, Mol % | | | | | | | | |
| | DCL | OLCL | DKT | HHP | DHP | MCL | MHP | MKT | DIPB |
| Recycle 0 | | | | | | | | | |
| Product | 0.4 | 0.3 | <0.1 | 1.7 | 14.8 | 8.2 | 40.0 | 1.1 | 33.7 |
| Net Prodn. | 0.4 | 0.3 | <0.1 | 1.7 | 14.8 | 8.2 | 40.0 | 1.1 | −66.3 |
| Recycle 1 and 2 | | | | | | | | | |
| Product | 0.4 | 0.5 | <0.1 | 2.7 | 9.0 | 9.8 | 48.1 | 1.5 | 27.9 |
| Charge | 0.3 | 0.2 | 0 | 0.5 | 1.4 | 7.8 | 39.3 | 1.1 | 49.4 |
| Net Prodn. | 0.1 | 0.3 | <0.1 | 2.2 | 7.6 | 2.0 | 8.8 | 0.4 | −21.5 |
| Recycle 3 | | | | | | | | | |
| Product | 0.6 | 0.7 | <0.1 | 3.0 | 13.6 | 10.2 | 45.6 | 1.6 | 24.6 |
| Charge | 0.3 | 0.4 | 0 | 0.8 | 1.1 | 9.1 | 44.7 | 1.4 | 42.2 |
| Net Prodn. | 0.3 | 0.3 | <0.1 | 2.2 | 12.5 | 1.1 | 0.9 | 0.2 | −17.6 |
| Recycle 4 | | | | | | | | | |
| Product | 0.7 | 0.8 | <0.1 | 3.5 | 19.7 | 9.9 | 42.3 | 1.6 | 21.5 |
| Charge | 0.5 | 0.6 | 0 | 1.3 | 2.5 | 8.7 | 39.0 | 1.5 | 46.1 |
| Net Prodn. | 0.2 | 0.2 | <0.1 | 2.2 | 17.2 | 1.2 | 3.3 | 0.1 | −24.6 |
| Recycle 5 | | | | | | | | | |
| Product | 0.9 | 2.0 | <0.1 | 3.9 | 10.6 | 13.3 | 45.1 | 1.3 | 22.9 |
| Charge | 0.6 | 0.7 | 0 | 1.3 | 2.6 | 9.0 | 39.6 | 1.5 | 44.7 |
| Net Prodn. | 0.3 | 1.3 | 0.1 | 2.6 | 8.0 | 4.3 | 5.5 | −0.2 | −21.8 |
| Recycle 6 | | | | | | | | | |
| Product | 1.1 | 2.0 | <0.1 | 4.2 | 10.6 | 12.7 | 41.0 | 1.1 | 27.2 |
| Charge | 0.7 | 1.2 | 0 | 1.5 | 0.7 | 10.1 | 36.7 | 0.9 | 48.2 |
| Net Prodn. | 0.4 | 0.8 | <0.1 | 2.7 | 9.9 | 2.6 | 4.3 | 0.2 | −21.0 |
| Recycle 7 | | | | | | | | | |
| Product | 1.1 | 2.3 | <0.1 | 4.8 | 10.6 | 12.1 | 43.2 | 1.5 | 24.4 |
| Charge | 1.0 | 2.1 | 0.02 | 2.3 | 2.7 | 11.8 | 37.7 | 1.2 | 41.2 |
| Net Prodn. | 0.1 | 0.2 | <0.08 | 2.5 | 7.9 | 0.3 | 5.5 | 0.3 | −16.8 |
| Recycle 8 | | | | | | | | | |

TABLE II-continued

| Composition of Product From Hydroperoxidation of CP m-DIPB | | | | | | | | | |
|---|---|---|---|---|---|---|---|---|---|
| | COMPONENTS, Mol % | | | | | | | | |
| | DCL | OLCL | DKT | HHP | DHP | MCL | MHP | MKT | DIPB |
| Product | 1.8 | 3.5 | 0.05 | 7.3 | 11.0 | 12.3 | 40.3 | 1.6 | 22.2 |
| Charge | 0.9 | 2.8 | 0 | 3.5 | 3.6 | 11.8 | 42.8 | 1.5 | 34.2 |
| Net Prodn. | 0.9 | 0.7 | 0.05 | 3.8 | 7.4 | 0.5 | −2.5 | 0.1 | −12.0 |
| Recycle 9 | | | | | | | | | |
| Product | 2.7 | 5.1 | 0.1 | 9.5 | 8.8 | 13.6 | 35.5 | 1.9 | 23.0 |
| Charge | 1.5 | 3.1 | 0 | 5.3 | 4.2 | 11.8 | 38.5 | 1.6 | 34.1 |
| Net Prodn. | 1.2 | 2.0 | 0.1 | 4.2 | 4.6 | 1.8 | −3.0 | 0.3 | −11.1 |
| Recycle 1-9 | | | | | | | | | |
| Tot. Prodn. | 3.5 | 5.8 | 0.7 | 22.4 | 75.1 | 13.8 | 22.8 | 1.4 | −146.4 |

Referring again to Example 1 and Table I, after 10 hydroperoxidation cycles, a total of 1120 g DHP/HHP product was obtained. From the HPLC data, it was calculated that for the nine cyclic operations the average mol % DHP in DHP+HHP product stream was 77%, excluding a small fraction of MHP which was also extracted into the product stream and should be removed from the product stream. It was also found that the average DIPB conversion was 42.4%. The ratio of product (DHP+HHP) v. recycle (MHP+DIPB) was 106.5:668–1:6.3 for the nine recycles. These values are low compared to those obtained in subsequent experiments using commercial m-DIPB. Based on subsequent work, described in Table IX below, for a 50% DIPB conversion, a ratio of 1:4 can be expected.

EXAMPLE 2

Hydroperoxidation Under Aqueous, Alkaline Conditions

In order to compare the results of Example 1 with aqueous, alkaline hydroperoxidation processes, four hydroperoxidation runs of CP m-DIPB in the presence of 2% aqueous sodium hydroxide solution were made using the same equipment. The results are shown in Table III. Since we did not use a pressure reactor, our experiments were limited to 1 atm and 100° C. The present commercial processes are believed to use higher temperatures and higher pressure.

The same one-liter flask was used for the hydroperoxidation of 600 g CP m-DIPB containing 30 g 56% m-MHP as initiator, in the presence of 65 g 2% aqueous sodium hydroxide. The subsequent hydroperoxidation with recycled MHP-DIPB was made with 650 g charge consisting of recycle MHP-DIPB and additional fresh m-DIPB.

The reaction temperature was raised to 95°–100° C. because the hydroperoxidation was much slower than in nonaqueous, non-alkaline media. The use of greater than 1 atm and higher than 100° C. was avoided in order to obtain data comparable with the data from nonaqueous hydroperoxidation.

Generally the same work-up procedure as described above was used. After the hydroperoxidation experiment of Recycle 0, the aqueous layer was separated and the products from the experiments with equal weights of 10% aqueous sodium hydroxide. The products from the experiments of Recycles 1 and 2 were extracted with equal weights of 4% aqueous sodium hydroxide. Extraction with 10% sodium hydroxide has produced a MHP/DIPB recycle that contains less DHP/HHP product. The composition of the hydroperoxidation products was calculated as before and shown in Table IV.

TABLE III

| DHP/HHP from CP m-DIPB in the Presence of Sodium Hydroxide | | | | | | | | | | |
|---|---|---|---|---|---|---|---|---|---|---|
| | Conditions | | | DHP/HHP | | MHP/DIPB Recycle | | DIPB | Net Production[2] | | |
| Recycle No. | time hrs. | temp. °C. | MHP[1] % | wt g | DHP[1] % | wt g | MHP[1] % | Conv.[2] % | DHP Mol % | HHP Mol % | DHP/DHP + HHP % |
| 0 | 36 | 90–99 | 58.0 | 87.0 | 79.7 | 595 | 43.8 | 63.1 | 6.5 | 4.9 | 57.0 |
| 1 | 28 | 95–100 | 59.0 | 93.6 | 75.7 | 542 | 47.4 | 45.4 | 5.9 | 6.5 | 47.6 |
| 2 | 32 | 99 | 54.0 | 83.9 | 64.9 | 569 | 42.7 | 44.3 | 3.2 | 6.4 | 33.3 |
| 3 | 32 | 100 | 45.2 | 56.6 | 67.4 | 453 | 36.1 | 35.6 | 3.2 | 3.0 | 51.6 |
| Av. 1-3 | | | 52.7 | 78.0 | 69.3 | 521 | 42.1 | 41.8 | 4.10 | 5.30 | 43.6 |

[1]By iodometric titration.
[2]Calculated from HPLC analysis.

TABLE IV

| Hydroperoxidation Products From CP m-DIPB in the Presence of 2% NaOH | | | | | | | | | |
|---|---|---|---|---|---|---|---|---|---|
| | COMPONENTS, Mol % | | | | | | | | |
| | DCL | OLCL | DKT | HHP | DHP | MCL | MHP | MKT | DIPB |
| Recycle 0 | | | | | | | | | |
| Product | 0.6 | 2.0 | <0.1 | 4.9 | 6.5 | 11.9 | 36.2 | 1.0 | 36.9 |
| Net Prodn. | 0.6 | 2.0 | <0.1 | 4.9 | 6.5 | 11.9 | 36.2 | 1.0 | −63.1 |
| Recycle 1 | | | | | | | | | |
| Product | 1.7 | 4.7 | <0.1 | 8.0 | 6.7 | 15.8 | 33.8 | 2.0 | 27.3 |
| Charge | 0.5 | 1.7 | 0 | 1.5 | 0.8 | 11.0 | 33.5 | 1.0 | 50.0 |
| Net Prodn. | 1.2 | 3.0 | <0.1 | 6.5 | 5.9 | 4.8 | 0.3 | 1.0 | −22.7 |
| Recycle 2 | | | | | | | | | |
| Product | 2.4 | 8.6 | <0.1 | 9.6 | 3.7 | 18.3 | 28.7 | 2.9 | 25.7 |
| Charge | 1.2 | 3.9 | 0 | 3.2 | 0.5 | 13.9 | 29.4 | 1.7 | 46.1 |

TABLE IV-continued
Hydroperoxidation Products From CP m-DIPB in the Presence of 2% NaOH

| | COMPONENTS, Mol % | | | | | | | | |
|---|---|---|---|---|---|---|---|---|---|
| | DCL | OLCL | DKT | HHP | DHP | MCL | MHP | MKT | DIPB |
| Net Prodn. | 1.2 | 4.7 | <0.1 | 6.4 | 3.2 | 4.4 | −0.7 | 1.2 | −20.4 |
| Recycle 3 | | | | | | | | | |
| Product | 4.0 | 10.8 | <0.1 | 6.7 | 3.7 | 23.3 | 25.1 | 3.5 | 22.8 |
| Charge | 1.9 | 7.5 | 0 | 3.5 | 0.7 | 17.9 | 30.2 | 2.9 | 35.4 |
| Net Prodn. | 2.1 | 3.3 | <0.1 | 3.2 | 3.0 | 5.4 | −5.1 | 0.6 | −12.6 |

Comparing the data of Tables I and III, it is apparent that the hydroperoxidation of m-DIPB in an anhydrous, non-alkaline media is better in many aspects than hydroperoxidation in the presence of dilute aqueous sodium hydroxide. First, the average final hydroperoxide concentration, calculated as wt % MHP from iodometric titrations was 76.7% for the nine cycles of nonaqueous hydroperoxidation, whereas the corresponding value for the three cycles in the presence of 2% aqueous sodium hydroxide was 52.7%. Second, the average % DHP of the DHP/HHP fraction, determined by iodometric titration, was 83.6% for the former and 69.3% for the latter. The value of DHP/DHP+HHP was 77.0% and 43.6%, respectively. It is concluded that hydroperoxidation in nonaqueous, non-alkaline media gives higher conversion of m-DIPB and better selectivity to the desired product. Comparing the hydroperoxidation of Recycle 0 (pure DIPB oxidation), the caustic extraction produces 87.0 g DHP/HHP fraction v. 161.0 g for the nonaqueous system. For the first three recycles, the average DHP/HHP product weighed 78.0 g v. 107.7 g for the nonaqueous system. In the oxidation process, the addition of water slows the process. It appears that the hydroperoxidation of m-DIPB in the presence of aqueous sodium hydroxide does in fact take place at a much slower rate than the hydroperoxidation in nonaqueous media.

Since hydroperoxidation of DIPB in the presence of aqueous sodium hydroxide is a slower reaction compared to that of the nonaqueous system, it would be expected to produce a lower quality DHP/HHP fraction. This, indeed, was observed. The average selectivity of DHP/HHP product from the aqueous sodium hydroxide runs was 43.6 mol % compared to 77.0 mol % for the nonaqueous system.

A possible, although somewhat over-simplified explanation of the results can be made as follows:

In the hydroperoxidation of DIPB to DHP, most of the DHP is produced in the chain propagation step of

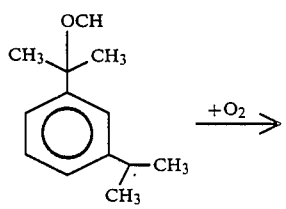

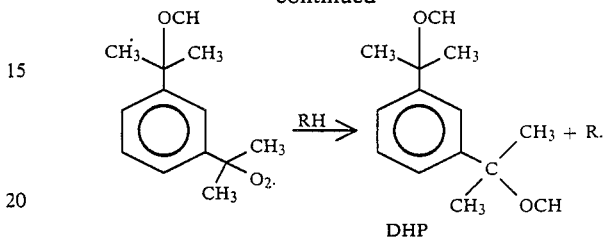

DHP

On the other hand, some HHP is produced from decomposition of DHP, e.g.,

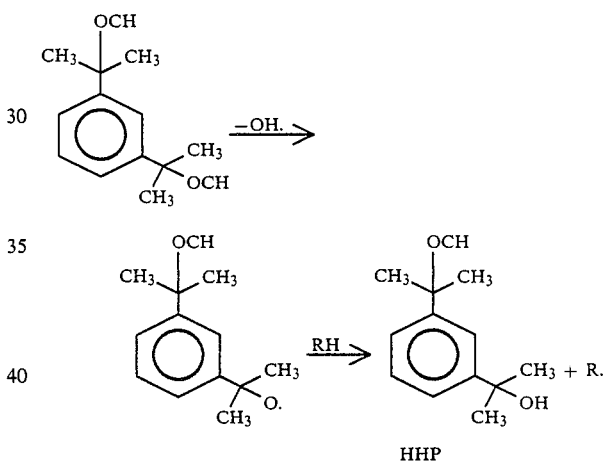

HHP

In the fast oxidation of DIPB, the chain propagation takes place rapidly and the production of DHP is favored. Only when the oxidation is slowed down, the decomposition of DHP becomes competitive, resulting in the production of more HHP.

As the concentration of HHP in the hydroperoxidation mixture increase, it can decompose to form secondary products, such as DCL and OLCL.

In order to compensate for the slower hydroperoxidation, commercial prior art processes employ higher reaction temperature and pressure, which in turn produce more by-products.

The nonaqueous hydroperoxidation process of the present invention permits operation at a lower reaction temperature, ideally about 85° C., and at a lower pressure, to achieve a high product selectivity. The oxidation process of the present invention can therefore be run in an open system without concern for pressure reaction vessels.

The process of the present invention produces its best results when the DIPB in the feed stream is comprised of major amounts of m-DIPB and less than about 6% o-DIPB. Commercially available DIPB, manufactured by alkylating benzene with propylene, usually contains all three isomers (o, m, and p). Since it is difficult to separate o-DIPB from m-DIPB by fractional distillation, it is important to determine the amount of the o-isomer tolerable in the DIPB feed.

Synthetic feeds of m-DIPB containing 2.5% and 5% o-DIPB were prepared and used in the cyclic hydroperoxidation study. Tables V and VI show the results of those experiments.

The aqueous sodium hydroxide solution containing the sodium salts of DHP and HHP was extracted twice at 80° C. with twice its volume of MIBK to isolate the DHP/HHP product. After evaporation of MIBK, the residue was analyzed by HPLC to determine its DHP/HHP content.

TABLE V

DHP/HHP from m-DIPB Containing 2.5% o-DIPB, 100% Recycle

| Recycle No. | Conditions time hrs. | Conditions temp. °C. | MHP[1] % | DHP/HHP wt g | DHP/HHP DHP[1] % | MHP/DIPB Recycle wt g | MHP/DIPB Recycle MHP[1] % | DIPB Conv.[2] % | Net Production[2] DHP Mol % | Net Production[2] HHP Mol % | Net Production[2] DHP/DHP + HHP % |
|---|---|---|---|---|---|---|---|---|---|---|---|
| 0 | 32 | 85–89 | 71.3 | 98.0 | 83.0 | 712 | 61.3 | 62.2 | 11.7 | 2.0 | 85.4 |
| 1 | 16 | 85–87 | 77.3 | 85.7 | 86.9 | 686 | 64.0 | 31.5 | 7.7 | 2.1 | 78.6 |
| 2 | 16 | 85–87 | 72.5 | 86.0 | 82.4 | 660 | 64.1 | 25.6 | 6.3 | 1.7 | 78.7 |
| 3 | 24 | 85–87 | 74.7 | 82.5 | 79.9 | 668 | 62.8 | 38.0 | 6.9 | 3.0 | 69.7 |
| 4 | 24 | 87–88 | 72.4 | 79.0 | 79.6 | 678 | 63.5 | 32.1 | 6.5 | 2.6 | 71.4 |
| 5 | 24 | 87 | 71.6 | 80.0 | 76.8 | 650 | 60.2 | 34.1 | 6.1 | 3.4 | 64.2 |
| 6 | 24 | 85–88 | 63.1 | 69.1 | 70.9 | 677 | 55.6 | 29.8 | 4.1 | 2.2 | 65.1 |
| 7 | 24 | 86–87 | 58.9 | 67.2 | 67.3 | 658 | 50.9 | 30.8 | 3.4 | 2.5 | 57.6 |
| 8 | 24 | 87–89 | 55.2 | 62.4 | 64.7 | 666 | 47.4 | 35.8 | 3.4 | 2.4 | 58.6 |
| 9 | 24 | 87–88 | 53.5 | 61.2 | 63.7 | 673 | N.D.[3] | 47.7 | 2.8 | 4.1 | 40.6 |
| 10 | 24, | 87–88 | 55.0 | 59.8 | 63.1 | 664 | 44.9 | 46.9 | 2.7 | 2.3 | 54.0 |
| Av. 1–10 | | | 65.4 | 73.3 | 73.5 | 668 | 57.0 | 35.2 | 4.99 | 2.63 | 65.5 |

[1]By iodometric titration.
[2]Calculated from HPLC analysis.
[3]Not determined.

TABLE VI

DHP/HHP from m-DIPB Containing 5.0% o-DIPB, 100% Recycle

| Recycle No. | Conditions time hrs. | Conditions temp. °C. | MHP % | DHP/HHP wt g | DHP/HHP DHP[1] % | MHP/DIPB Recycle wt g | MHP/DIPB Recycle MHP[1] % | DIPB Conv.[2] % | Net Production[2] DHP Mol % | Net Production[2] HHP Mol % | Net Production[2] DHP/DHP + HHP % |
|---|---|---|---|---|---|---|---|---|---|---|---|
| 0 | 40 | 80–96 | 75.4 | 47.6 | 80.7 | 305 | 60.3 | 67.0 | 11.2 | 7.8 | 59.0 |
| 1 | 24 | 85–91 | 64.3 | 30.5 | 80.0 | 338 | 59.9 | 37.8 | 5.4 | 3.7 | 59.3 |
| 2 | 24 | 85–92 | 71.7 | 40.6 | 74.1 | 269 | 61.2 | 43.6 | 6.1 | 3.8 | 61.6 |
| 3 | 24 | 88–92 | 59.4 | 32.8 | 68.8 | 273 | 51.5 | 38.9 | 3.5 | 2.9 | 54.7 |
| 4 | 24 | 87–90 | 53.4 | 34.1 | 62.7 | 269 | 43.9 | 41.3 | 3.1 | 1.1 | 73.8 |
| 5 | 32 | 86–90 | 52.9 | 32.4 | 63.9 | 276 | 43.2 | 43.0 | 3.3 | 2.4 | 57.9 |
| Av. 1–5 | | | 60.3 | 34.1 | 69.9 | 285 | 51.9 | 40.9 | 4.28 | 2.78 | 60.6 |

[1]By iodometric titration.
[2]Calculated from HPLC analysis.

EXAMPLE 3

Hydroperoxidation of m-DIPB Containing 2.5% o-DIPB

Hydroperoxidation of 750 g m-DIPB containing 2.5% o-DIPB was made in a one-liter flask at 85°–88° C. and 1 atm in nonaqueous, non-alkaline media using the same procedure as described earlier. In all experiments products were extracted once with an equal weight of 4% aqueous sodium hydroxide to separate the DHP/HHP fraction. The aqueous sodium hydroxide solution was extracted once with twice its weight and once with an equal weight of MIBK at 80° C. to recover the DHP/HHP fraction. Again, both the product and the recycle MHP/DIPB were analyzed by HPLC to determine their composition.

EXAMPLE 4

Hydroperoxidation of m-DIPB Containing 5% o-DIPB

Hydroperoxidation of 350 g m-DIPB containing 5% o-DIPB was made in a 500-ml flask at 85°–92° C. and 1 atm in nonaqueous, non-alkaline media for a period of about 24 hours, until the peroxide concentration was about 50–70% MHP. The product was extracted once with an equal weight of 4% aqueous sodium hydroxide.

Comparison of the data in Table V and VI with the data in Table I shows that:

(1.) Final hydroperoxide concentrations determined by iodometric titration are 10–15% higher in the cases of CP grade m-DIPB.

(2.) The DHP/HHP fractions obtained by caustic extraction contain less DHP (% DHP by titration) in the experiments with m-DIPB containing 2.5% and 5% o-DIPB. The average % DHP by titration was 83.6% for CP grade m-DIPB, 73.5% for m-DIPB containing 2.5% o-DIPB and 69.9% for m-DIPB containing 5% o-DIPB.

(3.) The CP grade m-DIPB runs gave highest % DHP/DHP+HHP values (average 77%) than the runs containing o-DIPB (65.5% and 60.6%, respectively).

Analysis of the hydroperoxidation by-products revealed that the presence of o-dIPB in DIPB feed increases the production of by-products, such as OLCL and MKT. The average mol % OLCL and MKT in the hydroperoxidation products of CP DIPB were 0.61% and 0.25%, respectively. The corresponding values with DIPB containing 5% o-DIPB were 2.75% and 0.58%, respectively.

It can be concluded, therefore, that a higher percentage of o-DIPB in the m-DIPB feed not only reduces the rates of m-DIPB hydroperoxidation, but also decreases the selectivity to the desirable products m-DHP and m-HHP.

EXAMPLE 5

Hydroperoxide of m-DIPB Containing Large Percentages of o-DIPB

The same procedure was used to hydroperoxidate m-DIPB containing 10%, 26%, 38%, and 43% o-DIPB, respectively, in the initial feed. The procedures were the same as those described for m-DIPB containing 5% o-DIPB, except that the percentage content of o-DIPB was altered accordingly. Technical grade DIPB containing 26% o-DIPB used in one experiment yielded recovered DIPB containing 38% o-DIPB which was used in another experiment. The recovered DIPB from the first recycle hydroperoxidation of the run containing 38% o-DIPB was found to contain 43% o-DIPB and was used as the charge for yet another experiment.

Hydroperoxidation of m-DIPB containing 10% and 26% o-isomer failed to produce satisfactory yields of m-DHP, even after only one recycle. There was a significant increase in the production of undesirable by-products, including DCL, OLCL, and MKT. It took 64 hours (twice as long as standard experiments) to obtain a 41% m-DIPB conversion when m-DIPB containing 26% o-isomer was used. In a similar experiment using m-DIPB containing 38% o-isomer, the DIPB conversion was only 26% after 64 hours. It was not possible to carry out the hydroperoxidation of the MHP/DIPB recycles from these two experiments. There was no increase in hydroperoxide concentration when the MHP/DIPB recycle obtained from the hydroperoxidation of m-DIPB containing 38% o-DIPB was heated at 85° C. in the presence of oxygen. The hydroperoxidation products from these two runs contained higher concentrations of by-products than the desirable DHP/HHP products, indicating a significant decomposition of DHP, HHP, and probably even MHP.

From the data it has been determined that when the percentage of o-isomer in DIPB exceeds about 6%, hydroperoxidation of DIPB becomes increasingly difficult under the same experimental conditions.

Additional experiments revealed that the hydroperoxidation of p-DIPB in nonaqueous, non-alkaline media behaved differently than the hydroperoxidation of m-DIPB. Hydroperoxidation of 100% p-DIPB under the conditions of the present invention showed no improvement over the yields of the prior art aqueous, alkaline hydroperoxidation processes. Moreover, and surprisingly, when the oxidation by-products, p-MHP/p-DIPB, were recycled to the feed stream for further hydroperoxidation, no hydroperoxides were produced under anhydrous, nonalkaline conditions.

Because o-DIPB is not oxidized during the hydroperoxidation of m-DIPB, it accumulates in the unreacted DIPB stream and the concentration of o-DIPB increases with the number of recycles of the DIPB.

It is generally recognized that it would be unrealistic to expect a commercial DIPB feed containing less than 1% o-isomer. Therefore, it is necessary to return a portion of the unreacted DIPB containing a higher percentage o-DIPB from the recycle stream and send it back to the alkylation plant for isomerization in order to prevent the build-up of o-DIPB which causes poor hydroperoxide yield. This can be done either by diverting a portion of recycle DIPB after each recycle or by displacing all unreacted DIPB after several recycles.

EXAMPLE 6

Hydroperoxidation of m-DIPB Containing 1.2% o-DIPB with an 80% Recycle of Recovered m-MHP and m-DIPB Hydroperoxidation of m-DIPB containing 1.2% o-DIPB was made using the same procedure as described above. The organic phase from the extraction with aqueous sodium hydroxide to remove DHP and HHP was washed with water, dried with 4A° sieves, and flash distilled in a Rinco evaporator to remove approximately 20% of the unreacted DIPB from the recycle stream. The flash distillate was found to contain as much as 30% MHP and a smaller quantity of MCL by GLC analysis.

The aqueous sodium hydroxide solution containing the sodium salts of DHP and HHP was extracted with MIBK to recover DHP and HHP fraction.

Results are shown in Table VII.

EXAMPLE 7

Hydroperoxidation of m-DIPB Containing 1.2% o-DIPB, with a 100% Recycle

Hydroperoxidation of each cycle was made with 350 g fresh DIPB feed and recycle MHP-DIPB mixture. After the hydroperoxidation, the product was extracted twice with equal weights of 4% aqueous sodium hydroxide to ensure a more complete extraction of m-DHP. The concentration of m-DHP in the recycle stream was determined to be less than 1%. The aqueous sodium hydroxide solution containing the sodium salts of m-DHP and m-HHP was extracted twice at 80° C. with twice its volume of MIBK to extract back m-DHP and m-HHP. After evaporation of MIBK solvent, the product was analyzed by HPLC.

Results are shown in Table VIII.

EXAMPLE 8

Hydroperoxidation of Commercial m-DIPB with an 80% Recycle of Recovered m-MHP and m-DIPB A 5-gallon sample of commercial m-DIPB was obtained and used without any treatment. Analysis of the commercial m-DIPB by GLC indicated a 98% purity of m-DIPB. Major impurities were: 0.8% o-DIPB, 0.4% p-DIPB, and less than 0.2% trimethylindane. A technical data sheet supplied by the manufacturer showed: >96% m-DIPB, 1.5% o-DIPB, and 0.5% p-DIPB.

Hydroperoxidation was made with 350 g feed comprising of about 30 mol % fresh DIPB, 25 mol % recycle DIPB and 45-50 mol % recycle MHP, and smaller amounts of MCL, HHP and OLCL. The product was extracted twice with equal weights of (approximately 400 ml) 4% aqueous sodium hydroxide to remove DHP and HHP. The organic phase was washed with 100 ml water, dried with 35 ml 4A° sieves, and filtered. Samples of the MHP/DIPB recycle were analyzed by HPLC.

The aqueous sodium hydroxide solution was extracted twice at 80° C. with twice its volume of MIBK (800 ml each) to recover the DHP/HHP product. The MHP/DIPB recycle was flash distilled in a Rinco evaporator to remove about 20% of unreacted DIPB from each recycle. The results are shown in Table IX.

TABLE VII

DHP/HHP From m-DIPB Containing 1.2% o-DIPB, 80% Recycle

| Recycle No. | Conditions time hrs. | Conditions temp. °C. | MHP[1] % | DHP/HHP wt g | DHP/HHP DHP[1] % | MHP/DIPB Recycle wt g | MHP/DIPB Recycle MHP[1] % | MHP/DIPB Recycle % o-in DIPB | DIPB Conv.[2] % | Net Production[2] DHP Mol % | Net Production[2] HHP Mol % | Net Production[2] DHP/DHP + HHP % |
|---|---|---|---|---|---|---|---|---|---|---|---|---|
| 0 | 40 | 87–89 | 80.1 | 76.4 | 84.7 | 281 | 61.1 | N.D.[3] | 63.6 | 14.0 | 4.0 | 77.8 |
| 1 | 24 | 86–87 | 78.0 | 66.3 | 80.8 | 307 | 53.4 | N.D.[3] | 50.1 | 9.7 | 3.2 | 75.2 |
| 2 | 24 | 86–87 | 73.4 | 64.4 | 76.7 | 308 | 56.7 | N.D.[3] | 44.3 | 9.6 | 3.2 | 75.0 |
| 3 | 24 | 86–87 | 78.8 | 69.9 | 81.9 | 304 | 57.6 | N.D.[3] | 50.3 | 11.4 | 4.4 | 72.2 |
| 4 | 24 | 86 | 60.5 | 49.6 | 62.7 | 318 | 45.9 | N.D.[3] | 42.6 | 4.9 | 2.9 | 62.8 |
| 5 | 24 | 85 | 54.4 | 47.2 | 68.7 | 314 | 43.9 | N.D.[3] | 30.1 | 4.8 | 2.7 | 64.0 |
| 6 | 24 | 85 | 63.0 | 55.7 | 75.5 | 314 | 48.3 | N.D.[3] | 44.9 | 7.7 | 4.0 | 65.8 |
| 7 | 24 | 85 | 69.9 | 63.3 | 76.9 | 308 | 52.3 | N.D.[3] | 46.8 | 8.8 | 4.2 | 67.7 |
| 8 | 24 | 85 | 76.3 | 66.9 | 82.1 | 304 | 56.7 | N.D.[3] | 46.4 | 10.4 | 3.1 | 77.0 |
| 9 | 24 | 85 | 75.1 | 68.4 | 80.7 | 303 | 52.7 | N.D.[3] | 47.2 | 10.6 | 3.1 | 77.4 |
| 10 | 24 | 85 | 78.1 | 60.3 | 83.0 | 311 | 60.3 | 4.5 | 41.7 | 9.3 | 2.8 | 76.9 |
| Av. 1-10 | | | 70.8 | 61.2 | 76.9 | 309 | 52.8 | | 44.4 | 8.72 | 3.36 | 72.2 |

[1]By iodometric titration.
[2]Calculated from HPLC analysis.
[3]Not determined.

TABLE VIII

DHP/HHP From m-DIPB Containing 1.2% o-DIPB, 100% Recycle

| Recycle No. | Conditions time hrs. | Conditions temp. °C. | MHP[1] % | DHP/HHP wt g | DHP/HHP DHP[1] % | MHP/DIPB Recycle wt g | MHP/DIPB Recycle MHP[1] % | MHP/DIPB Recycle % o-in DIPB | DIPB Conv.[2] % | Net Production[2] DHP Mol % | Net Production[2] HHP Mol % | Net Production[2] DHP/DHP + HHP % |
|---|---|---|---|---|---|---|---|---|---|---|---|---|
| 0 | 40 | 85–87 | 78.1 | 65.6 | 83.2 | 283 | 55.0 | N.D.[3] | 63.2 | 12.0 | 3.3 | 78.4 |
| 1 | 24 | 85–87 | 81.2 | 70.0 | 82.9 | 302 | 62.1 | N.D.[3] | 46.8 | 11.5 | 3.7 | 75.7 |
| 2 | 24 | 87 | 70.6 | 60.5 | 75.5 | 305 | 54.0 | N.D.[3] | 39.9 | 8.2 | 4.3 | 65.6 |
| 3 | 24 | 87–89 | 70.4 | 62.3 | 76.5 | 304 | 53.4 | N.D.[3] | 40.8 | 8.6 | 4.7 | 64.7 |
| 4 | 24 | 89 | 64.8 | 63.1 | 70.0 | 303 | 52.1 | N.D.[3] | 44.4 | 7.8 | 6.0 | 56.5 |
| 5 | 24 | 87–88 | 62.1 | 67.5 | 71.4 | 298 | 50.8 | N.D.[3] | 47.0 | 7.8 | 5.9 | 56.9 |
| 6 | 24 | 87 | 64.3 | 65.3 | 70.7 | 301 | 49.8 | N.D.[3] | 43.2 | 7.5 | 6.0 | 55.6 |
| 7 | 24 | 87 | 64.1 | 63.4 | 67.2 | 300 | 49.3 | N.D.[3] | 46.5 | 6.5 | 5.1 | 48.2 |
| 8 | 24 | 87 | 55.1 | 58.2 | 62.8 | 305 | 44.7 | N.D.[3] | 44.3 | 4.5 | 4.7 | 48.9 |
| 9 | 32 | 85–87 | 36.1 | 47.4 | 32.9 | 310 | 28.5 | 9.3 | 40.2 | 2.3 | 2.1 | 52.3 |
| Av. 1-7 | | | 68.2 | 64.6 | 73.5 | 302 | 53.1 | | 44.1 | 8.27 | 5.10 | 61.9 |
| Av. 1-9 | | | 63.2 | 62.0 | 67.8 | 303 | 49.4 | | 43.7 | 7.19 | 4.72 | 60.4 |

[1]By iodometric titration.
[2]Calculated from HPLC analysis.
[3]Not determined.

TABLE IX

DHP/HHP From Commerical m-DIPB, 80% Recycle

| Recycle No. | Conditions time hrs. | Conditions temp. °C. | MHP[1] % | DHP/HHP wt g | DHP/HHP DHP[1] % | MHP/DIPB Recycle wt g | MHP/DIPB Recycle MHP[1] % | MHP/DIPB Recycle % o-in DIPB |
|---|---|---|---|---|---|---|---|---|
| 0 | 40 | 85–86 | 71.2 | 75.6 | 81.4 | 280 | 60.3 | N.D.[4] |
| 1 | 24 | 85 | 67.9 | 48.7 | 82.1 | 319 | 56.0 | 3.0 |
| 2 | 24 | 85 | 72.8 | 59.2 | 83.6 | 314 | 58.8 | 3.3 |
| 3 | 32 | 85 | 86.0 | 74.4 | 86.9 | 303 | 62.6 | 4.2 |
| 4 | 32 | 85 | 80.2 | 72.2 | 84.8 | 300 | 61.6 | 4.0 |
| 5 | 32 | 85 | 81.4 | 73.4 | 85.1 | 302 | 61.7 | 5.2 |
| 6 | 32 | 85 | 75.2 | 75.8 | 84.6 | 298 | 60.4 | 5.4 |
| 7 | 32 | 85 | 81.1 | 76.3 | 84.9 | 298 | 59.7 | 5.1 |
| 8 | 32 | 85 | 83.4 | 81.8 | 83.1 | 305 | 59.9 | 4.6 |
| 9 | 32 | 85 | 78.1 | 76.6 | 84.9 | 296 | 58.9 | 4.3 |
| Av. 1-9 | | | 78.5 | 70.9 | 84.4 | 304 | 60.0 | 4.3 |

| Recycle No | Conditions time hrs. | Conditions temp. °C. | DIPB Conv.[2] % | Net Production[2] DHP Mol % | Net Production[2] HHP Mol % | Net Production[2] DHP/DHP + HHP % | Yield,[3] % |
|---|---|---|---|---|---|---|---|
| 0 | 40 | 85–86 | 75.6 | 15.3 | 3.0 | 83.6 | 93.4 |
| 1 | 24 | 85 | 34.2 | 7.2 | 2.4 | 75.0 | 92.3 |
| 2 | 24 | 85 | 45.0 | 8.9 | 3.6 | 71.2 | 94.7 |
| 3 | 32 | 85 | 65.8 | 14.7 | 3.7 | 79.9 | 92.0 |
| 4 | 32 | 85 | 50.5 | 10.3 | 3.9 | 72.5 | 95.3 |
| 5 | 32 | 85 | 57.9 | 12.7 | 4.1 | 75.6 | 93.9 |
| 6 | 32 | 85 | 53.1 | 11.3 | 4.0 | 73.9 | 95.6 |
| 7 | 32 | 85 | 52.2 | 12.3 | 4.5 | 73.2 | 87.5 |
| 8 | 32 | 85 | 54.9 | 13.2 | 3.7 | 78.1 | 90.9 |
| 9 | 32 | 85 | 52.9 | 11.6 | 4.2 | 73.4 | 92.4 |

TABLE IX-continued

| DHP/HHP From Commerical m-DIPB, 80% Recycle | | | | | |
|---|---|---|---|---|---|
| Av. 1-9 | 85 | 51.8 | 11.4 | 3.8 | 75.0 | 92.8 |

[1] By iodometric titration.
[2] Calculated from HPLC analysis.
[3] Yield = $\frac{\text{Mol DHP} + \text{Mol HHP} \times 100}{\text{DIPB conv.} - \text{Mol MHP} - \text{Mol MCL}}$
[4] Not determined.

Hydroperoxidation of m-DIPB containing 1.2% o-isomer with 80% recycle of unreacted DIPB produced encouraging results as shown in Table VII. As the recycles progressed the decreases in % final MHP was less significant and the average weight of the DHP/HHP fraction was 61.2 g for the 10 cycles. More importantly, the average % DHP by titration of the DHP/HHP fraction was 76.9%, compared to 67.8% for the 100% recycle series, as shown in Table VIII. Diverting 20% of the recycle DIPB was observed to have raised the % DHP in the DHP/HHP product nearly 10%.

The MHP-DIPB fraction recovered from Recycle 9 (See Table VIII) was distilled to recover unreacted m-DIPB. Analysis of the recovered m-DIPB by GLC showed it to have 9.3% o-isomer and 4.8% 1,1,3-trimethylindane (TMI) as impurities. It supports the conclusion that the deterioration in m-DIPB hydroperoxidation with increasing recycles is caused by the build-up of o-DIPB concentration in the recycles. Similarly, the mol % DHP/DHP+HHP determined by HPLC was 72.2%, compared to 60.4%. Therefore, it is concluded that hydroperoxidation with 80% recycle of DIPB produces higher selectivity to desirable hydroperoxides (DHP+HHP).

It was concluded, based on the data of Examples 6 and 7, that m-DIPB is hydroperoxidized to a 3:1 mixture of m-DHP/m-HHP product in about 95% selectivity in a cyclic batch operation at 85° C. and 1 atm, at a DIPB conversion of 45-55% per cycle, provided the concentration of o-isomers in the recycle is kept below about 6%.

In the cyclic batch hydroperoxidation of Example 8 using commercial m-DIPB, a feed containing 50 mol % m-DIPB, 40 mol % MHP, 5 mol % MCL, and 2.5 mol % was oxidized to produce 25 mol % of m-DHP/m-HHP product and 25 mol % unreacted m-DIPB of the 25 mol % recovered DIPB, 20 mol % was recycled to the hydroperoxidation and 5 mol % was removed for returning to the manufacturer. Results shown in Table IX show that there was practically no change in final MHP concentration after nine cycles of hydroperoxidation. The slight variation in final MHP concentration was probably caused by temperature fluctuation since a constant temperature bath was not used. Neither the DHP concentration of DHP/HHP fraction determined by titration nor the value of % DHP/DHP+HHP determined by HPLC analysis changed very much with the number of recycles. Most importantly, the concentration of o-DIPB in the recycle DIPB stream remained in the range of 3.0 to 5.4%, well below the maximum allowable impurity level of 6.0%. In other words, hydroperoxidation of m-DIPB is not deteriorated unless there is a build-up of o-DIPB concentration in the recycle stream. The average yield of DHP/HHP product was 92.8% calculated from the equation:

$$\text{Yield} = \frac{\text{Mol } DHP + \text{Mol } HHP \times 100}{DIPB \text{ conv.} - \text{Mol } MHP - \text{Mol } MCL}$$

Conversion of m-HHP to m-DHP

Hydroperoxidation of m-DIPB produces almost a 3:1 mixture of m-DHP/m-HHP. Unfortunately this product cannot be used to obtain good resorcinol yield. Almost all acid-catalyzed decompositions of m-DHP to resorcinol require the use of pure DHP. Since there is no practical way to separate HHP from DHP and HHP is also decomposed by an acidic catalyst, a way must be developed to convert HHP to DHP before the acid-catalyzed decomposition is made. A modified version of the process described in U.S. Pat. Nos. 4,238,570 and 4,267,387 was determined to be advantageous. The prior art process uses a heterogenous system of hydrogen peroxide in an aromatic hydrocarbon solvent and stresses the need to continuously remove co-product water by azeotropic distillation.

The hydrogen peroxide oxidation step of the present invention does not continuously remove water. It has been determined to be advantageous to evaporate the MIBK from the m-DHP/m-HHP fraction because the presence of MIBK requires the use of excess amounts of hydrogen peroxide to overcome the reaction between MIBK and hydrogen peroxide. Following evaporation of MIBK, the m-DHP/m-HHP fraction is preferably dissolved in toluene which does not necessitate the use of excess hydrogen peroxide. Stoichiometric amounts of hydrogen peroxide can be used in the instant process. Concentrations as low as 13-18% hydrogen peroxide have been used to yield 88.3% resorcinol on DHP+HHP. Higher concentrations can also be used, as in the Example below. Small, effective amounts of sulfuric acid are preferably added as a catalyst.

EXAMPLE 9

In a 100 ml 3-neck flask equipped with a stirrer, thermometer, and reflux condenser was placed 7.5 g of DHP/HHP mixture dissolved in 75 ml toluene. The flask was heated in a water bath maintained at 40° C. with stirring. An aqueous solution consisting of 2.55 g 50% hydrogen peroxide, 0.953 g 96% sulfuric acid, and 3.552 g water, which is equal to 1.5 M [$H_2SO_4$], 6.0 M [$H_2O_2$], and 400% excess hydrogen peroxide based on 21 mol % HHP in DHP/HHP mixture, was added to the flask and the mixture was stirred vigorously at 40° C. for one hour. It was cooled to room temperature and the mixture was transferred to a sep-funnel. The decomposition product was washed with 2 ml water and neutralized with 5 drops of 10% sodium carbonate ($Na_2CO_3$). It was dried with 5 g 4A° molecular sieves at room temperature for 45 min and the sieves were removed by filtration. The toluene solution was put back in the 3-neck flask and heated to 50° C. The water bath was removed and a boron trifluoride catalyst was introduced below the liquid surface until a vigorous exothermic reaction took place. If necessary, the flask was cooled with an ice-water bath to keep the temperature at 50° C. After the reaction had subsided, the flask was heated in a water bath at 50° C. for 45 min to complete the decomposition. After cooling to room temperature, the reaction mixture was transferred to a sep-funnel and 50 ml water was added. A 10% aqueous sodium carbonate solution was added dropwise until the aqueous phase became neutral after vigorous shaking. The toluene phase was separated and the aqueous phase was extracted three times with 50 ml each of ether to recover resorcinol. The combined ether and toluene solutions were evaporated to dryness and the residue was analyzed by HPLC to determine its resorcinol content.

TABLE X

Resorcinol Yields With and Without $H_2O_2$ Oxidation of DHP/HHP

| Run No. | % DHP Purity | % Yield w/o $H_2O_2$ Oxidn. (on DHP) | % Yield w/o $H_2O_2$ Oxidn. (on DHP + HHP) | % Yield w/o $H_2O_2$ Oxidn. (on DHP) | % Yield w/o $H_2O_2$ Oxidn. (on DHP + HHP) |
|---|---|---|---|---|---|
| 1 | 100.0 | 96.6 | 96.6 | 93.1 | 93.1 |
| 2 | 81.0 | 82.1 | 70.3 | 103.6 | 88.6 |
| 3 | 79.4 | 82.4 | 70.7 | 104.6 | 89.8 |
| 4 | 75.1 | 74.4 | 60.0 | 112.1 | 92.0 |
| 5 | 70.0 | 70.4 | 54.0 | 112.3 | 86.2 |
| 6 | 54.1 | 76.6 | 48.5 | 125.8 | 79.5 |
| 7 | 67.5 | 77.4 | 58.5 | 116.3 | 87.8 |
| 8 | 68.9 | 76.9 | 57.9 | 120.5 | 90.8 |
| 9 | 67.4 | 85.0 | 61.8 | 116.9 | 85.1 |
| Average[1] | 76.7 | 78.4 | 61.9 | 112.3 | 88.6 |

[1]Average of Runs 2-5 and 7-9 (Runs 1 and 6 were excluded since they were not considered to be typical DHP purities in a commercial operation.)

Run 1 of Table X (93.1% on DHP) represents the maximum resorcinol yield since the concentration of HHP in the DHP/HHP sample is approximately zero. The results of Table X show a significant increase in resorcinol yield after the hydrogen peroxide treatment. The resorcinol yield on DHP+HHP varies from 79.5 to 92% indicating 70 to 95% of the HHP in the original feed had been converted to DHP by the hydrogen peroxide treatment. Since the feed of these experiments was obtained directly from the hydroperoxidation of m-DIPB and contained impurities which cannot be oxidized to DHP, these resorcinol yields can be considered as being close to the maximum attainable yields.

The recovered hydrogen peroxide solution is mixed with 50% hydrogen peroxide stock solution to prepare the 6.0 M hydrogen peroxide feed for the next oxidation of DHP/HHP mixture. The oxidized DHP/HHP product in toluene can be dried by any suitable known procedure such as with a molecular sieve. It has been determined that water removal is important to the decomposition of m-DHP with boron trifluoride as shown in Example 10 and Table XI.

Decomposition of m-DHP To Resorcinol

The last step of the 3-step hydroperoxidation process is the decomposition of m-DHP in the presence of acidic catalysts to co-produce resorcinol and acetone. In the current commercial process, this is done in the presence of a small amount, in the percent composition range, of a Bronsted acid catalyst, generally a mineral acid, such as sulfuric acid. The decomposition product, usually dissolved in an organic solvent, is neutralized with dilute alkali and then distilled to obtain crude resorcinol.

An improved method for the decomposition of m-DHP using a Lewis acid catalyst selected from the group consisting of boron trifluoride and stannic chloride, preferably anhydrous boron trifluoride or its complexes, is provided by the present invention. From the results presented in Table XII it is shown that the activity of the boron trifluoride catalyst is higher than the conventional catalysts. This is a definite advantage for using $BF_3$ in the decomposition of m-DHP. The decomposition of m-DHP has been achieved using significantly smaller amounts of catalyst, e.g. 10 to 100 ppm, and as low as 10 to 50 ppm, at a temperature of about 50° C.

The m-DHP fraction must be dried as described above prior to decomposition with boron trifluoride. It has been observed that the higher the moisture content, the greater amount of catalyst is required. Water decreases the activity of boron trifluoride by producing a less active catalytic species which favors the production of undesirable decomposition products. An approximate upper limit of water content has been determined to be 0.1 wt %.

EXAMPLE 10

In a 200 ml flask was placed 75 ml of solvent (toluene or MIBK) and 15 ml of an aqueous solution containing 6 M $H_2O_2$ and 1.5 M $H_2SO_4$. After stirring at room temperature for 30 min., the aqueous phase was separated and the solvent was dried with 5 g drying agent (anhydrous $Na_2SO_4$ or 4 A° Molecular Sieves) at 50° C. for 30 min. The solvent was used to decompose 7.5 g of m-DHP (>90% purity) using as much $BF_3$-$Et_2O$ catalyst as needed to start the decomposition of DHP at 50° C. After one hour of reaction, the reaction mixture was cooled at room temperature and the solvent was evaporated at 40° C. and 4 mm pressure using a Rinco evaporator. The recovered solid was weighed and analyzed by HPLC for resorcinol. Resorcinol yield was calculated from the sample weight and resorcinol wt. % in the HPLC analysis. The results are shown in Table XI.

TABLE XI

Effect of $H_2O$ in Solvent on Resorcinol Yield

| Run Nos. | Solvent | Drying Agent | % $H_2O$ in Solvent | Amount $BF_3$-$Et_2O$ used (ml) | Resorcinol yield, % |
|---|---|---|---|---|---|
| 1 | Toluene | none | 0.029 | 0.035 | 75 |
| 2 | Toluene | $Na_2SO_4$ | 0.024 | 0.030 | 78 |
| 3 | Toluene | 4A Sieves | 0.012 | 0.025 | 83 |
| 4 | MIBK | none | 2.5 | 0.20 | 52 |
| 5 | MIBK | $Na_2SO_4$ | 1.8 | 0.30 | 54 |
| 6 | MIBK | 4A Sieves | 0.065 | 0.030 | 80 |

[1]Determined by Karl Fisher method.

EXAMPLE 11

In a 100 ml 3-neck flask equipped with a stirrer, thermometer, and reflux condenser was placed 15 g of m-DHP dissolved in 75 ml of MIBK (or toluene). The flask was heated in a water-bath maintained at 50° C. with stirring. Using a microliter syringe, 25 microliters of boron trifluoride etherate ($BF_3$.$Et_2O$) was charged to the flask to start the decomposition of m-DHP to resorcinol. After one hour of reaction, the reaction mixture was cooled to room temperature and a small sample was analyzed by GLC. The reaction mixture was immediately transferred to a Rinco evaporator and the solvent was evaporated at 40° C. and 4 mm pressure (higher pressure if toluene is used as solvent). The recovered solid was weighed and analyzed by HPLC. Resorcinol yield was calculated from the sample weight and resorcinol wt % in the HPLC analysis.

Table XII shows the yields of resorcinol from the decomposition of m-DHP containing only a small percentage of m-HHP.

TABLE XII

Effect of Solvent and m-DHP Purity on Resorcinol Yield

| Run No. | % m-DHP[1] | Solvent | Amt. BF$_3$[2] μl. | Resorcinol Yield, % by GLC | by HPLC |
|---|---|---|---|---|---|
| 1 | 95 | MIBK | 25 | 101.1 | 98.0 |
| 2 | 90 | Tol | 25 | 95.9 | 95.9 |
| 3 | 80 | MIBK | 30 | 85.3 | 84.3 |
| 4 | 70 | MIBK | 40 | 77.9 | 72.7 |
| 5 | 90 | Tol | 50[3] | 61.1 | ND[4] |

[1]Percent m-DHP from iodometric titration.
[2]BF$_3$ etherate.
[3]Ninety-six (96) % H$_2$SO$_4$ was used in this experiment.
[4]Not determined.

Analysis of the decomposition product, either by CLG or HPLC, indicates a high selectivity to resorcinol. In the prior art hydroperoxidation process, it is difficult to obtain resorcinol in high purity. The advantage of using a boron trifluoride catalyst is evident. Even with less pure m-DHP (other components are m-HHP and m-MHP), resorcinol yields are still better than the decomposition of pure m-DHP (90%) with a sulfuric acid catalyst.

Table XIII summarizes the decomposition of m-DHP/m-HHP mixtures obtained directly from the caustic extraction of m-DIPB hydroperoxidation products. Yields of resorcinol based on m-DHP present were 21.7% to 33.7% lower than the theoretical yields. In general, when low purity m-DHP is decomposed, there is a lower resorcinol yield. This is not surprising because it usually takes 2 to 3 days to finish the work-up procedure, and resorcinol is a very reactive compound and probably forms secondary products, especially in the presence of an acidic catalyst.

TABLE XIII

Variation of Resorcinol Yield with m-DHP Purity

| Run No | m-DHP Purity,[1] mol % | Product Purity, % Resorcinol | % Yield (on DHP) |
|---|---|---|---|
| 1 | 100 | 86.9 | 91.5 |
| 2 | 94 | 75.0 | 82.7 |
| 3 | 78 | 48.0 | 72.7 |
| 4 | 74 | 31.0 | 54.7 |
| 5 | 72 | 30.0 | 54.6 |
| 6 | 68 | 22.5 | 34.3 |
| 7 | 52 | 21.5 | 49.3 |

[1]Mol % m-DHP determined by HPLC.

EXAMPLE 12

The following procedure was used to obtain more accurate data for the decomposition of m-DHP/m-HHP mixture using a boron trifluoride catalyst.

In a 100 ml 3-neck flask equipped with a stirrer, thermometer, and reflux condensor was placed 7.5 g m-DHP/m-HHP mixture dissolved in 75 ml toluene. The flask was heated in a water-bath to 50° C. with stirring. After removing the water-bath, 15–100 microliters of boron trifluoride etherate was introduced below the liquid surface, using a microliter syringe and a long needle. The flask was cooled with an ice-water bath to remove the exothermic heat of reaction. The flask was maintained at 50° C. for 45 minutes and then cooled to room temperature. The contents were transferred to a 150 ml sep-funnel and 50 ml water was added. After shaking for a few minutes, a 10% aqueous sodium carbonate solution was added dropwise until the pH of the aqueous phase was neutral (pH=7). The toluene phase was separated and the aqueous phase was extracted three times with 50 ml portions of ether. The combined ether and toluene solutions were evaporated to dryness and the residue was weighed and analyzed by HPLC, using a standard technique for analysis of resorcinol.

Table XIV shows the effect of catalyst neutralization (with 10% aqueous Na$_2$CO$_3$) on the yields of resorcinol using boron trifluoride as catalyst. It shows not only that the yields are increased by neutralizing the boron trifluoride catalyst immediately after the decomposition of m-DHP, but also that if acetone is used as solvent and boron trifluoride catalyst is not removed after the decomposition, there will be a large reduction in resorcinol yield indicating a possible reaction between resorcinol and acetone.

TABLE XIV

Effect of Catalyst Neutralization on Resorcinol Yield

| Run No | m-DHP,[1] % | Solvent | Product Purity, % Resorcinol | Yield, (on DHP) | % Catalyst Neutralization |
|---|---|---|---|---|---|
| 1 | 100 | Toluene | 86.9 | 91.5 | w/o neut. |
| 2 | 100 | Toluene | 85.5 | 85.5[2] | w neut. |
| 3 | 100 | Acetone | 65.5 | 75.0 | w/o neut. |
| 4 | 100 | Acetone | 90.0 | 90.1 | w neut. |
| 5 | 74 | Toluene | 21.5 | 36.9 | w/o neut. |
| 6 | 74 | Toluene | 29.0 | 50.3 | w neut. |
| 7 | 74 | Acetone | 10.5 | 19.9 | w/o neut. |
| 8 | 74 | Acetone | 44.5 | 72.6 | w neut. |

[1]% m-DHP was determined by HPLC.
[2]The lower yield with neutralization may be due to mechanial losses during the washing step.

In order to minimize uncertainties in resorcinol yield due to the loss of resorcinol during work-up of m-DHP decomposition products, the following GLC analysis method was used to obtain improved resorcinol yields. Results are shown in Table XV.

EXAMPLE 13

The decomposition of 7.5 g m-DHP/m-HHP sample in 75 ml solvent with a small amount of boron trifluoride etherate was made using the same procedure as described. After the decomposition, the solution was cooled to room temperature with an ice-water bath. The product was transferred to a 250 ml volumetric flask and diluted to 250 ml with toluene. An external standard was prepared by dissolving a weighed quantity of pure resorcinol (usually 13.5 g) in approximately 10 ml acetone and then diluting it to 250 ml with toluene. The two solutions were analyzed by GLC using the response factor of the external standard to determine the weight % resorcinol. A 10'×⅛" SS column packed with 10% OV17 at 210° C. was used for GLC analysis.

TABLE XV

Decomposition of m-DHP with BF$_3$ Catalyst

| Run No. | % DHP in Sample[1] | Solvent | Resorcinol Yield,[2] mol % (on DHP) |
|---|---|---|---|
| 1 | 100.0 | MIBK | 96.6 |
| 2 | 81.0 | MIBK | 82.1 |
| 3 | 79.4 | MIBK | 82.4 |
| 4 | 75.1 | MIBK | 74.4 |
| 5 | 70.0 | MIBK | 70.4 |
| 6 | 54.1 | MIBK | 76.6 |
| 7 | 100.0 | Toluene | 96.4 |
| 8 | 67.5 | Toluene | 77.4 |
| 9 | 68.9 | Toluene | 76.9 |

TABLE XV-continued

Decomposition of m-DHP with BF₃ Catalyst

| Run No. | % DHP in Sample[1] | Solvent | Resorcinol Yield,[2] mol % (on DHP) |
|---|---|---|---|
| 10 | 67.4 | Toluene | 85.0 |

[1]Percent DHP was determined by HPLC analysis. Its accuracy was estimated to be ±2%.
[2]Based on GLC analysis.

Compared to currently available technology, the results of m-DHP decomposition catalyzed by boron trifluoride (See Table XV) are excellent. The % resorcinol yields based on % DHP present in the sample are 70.4% to 96.6% depending on the purity of m-DHP. The yields are higher when toluene is used as solvent, indicating a possible reaction between resorcinol and MIBK. These yields, however, are still higher than those when concentrated sulfuric acid is used as catalyst. Run 5 of Table XII gave a 61.1% resorcinol yield when 50 microliters of 96% sulfuric acid was used as catalyst, compared to a 95.9% yield when 25 microliter of boron trifluoride was used.

For comparison, decomposition of m-DHP in the presence of several different Lewis acid catalysts was investigated and the results are show in Table XVI. Both boron trifluoride (BF₃) and stannic chloride (SnCl₄) gave the best yields. Ferric chloride (FeCl₃) also gave an acceptable yield. Boron trifluoride is, however, preferred in view of the potential environmental problems associated with stannic chloride. Decompositions with aluminum chloride (AlCl₃) gave a very poor yield of resorcinol. Therefore, not all Lewis acids are good catalysts for the decomposition of m-DHP.

TABLE XVI

Evaluation of Lewis Acids for m-DHP Decomposition

| Run No. | DHP, Purity % | Solvent | Catalyst Type | Amount | Resorcinol Yield, % (on DHP) |
|---|---|---|---|---|---|
| 1 | 100 | Toluene | BF₃[2] | 20 μl | 96.5 |
| 2 | 100 | Toluene | SnCl₄ | 25 μl | 100.6 |
| 3 | 100 | Toluene | FeCl₁₃ | 0.05 g | 86.7 |
| 4 | 100 | Toluene | AlCl₃ | 0.5 g | 14.0 |
| 5 | 100 | Toluene | SO₃ | 1 | 88.0 |
| 6 | 81 | MIBK | BF₃[2] | 170 μl | 82.1 |
| 7 | 81 | Toluene | SnCl₄ | 100 μl | 79.0 |

[1]Used 3.8 g of a 0.7% SO₃ in acetone.
[2]BF₃ etherate.

Another advantage of the boron trifluoride catalyst is its low activity in promoting the secondary reactions of the resorcinol that is produced. A minute quantity of boron trifluoride used to decompose m-DHP is not sufficient to promote the reaction between resorcinol and isopropenylphenol, for example. In addition, the boron trifluoride catalyst can readily be removed from the organic phase by washing with a small amount of aqueous sodium hydroxide. Thus, the crude resorcinol obtained by the boron trifluoride-catalyzed decomposition of m-DHP does not require a specific purification process. This is considered to be an advantage of the boron trifluoride-catalyzed decomposition of m-DHP provided by the process of the present invention.

What is claimed is:

1. A process for the preparation of resorcinol comprising the steps of:
   oxidizing diisopropylbenzene under anhydrous, non-alkaline conditions with oxygen, wherein said diisopropylbenzene is comprised of major amount of the m-isomer and less than about six percent of the o-isomer;
   extracting a mixture of m-diisopropylbenzene dihydroperoxide and m-diisopropylbenzene hydroxyhydroperoxide from the products of said oxidizing step with dilute sodium hydroxide;
   re-extracting said mixture from said sodium hydroxide with an organic solvent; and
   decomposing substantially anhydrous m-diisopropylbenzene dihydroperoxide in the presence of an effective amount of a catalyst selected from the group consisting of boron trifluoride, ferric chloride and stannic chloride, to produce a decomposition product containing resorcinol.

2. The process of claim 1 further comprising the steps of converting said m-diisopropylbenzene hydroxyhydroperoxide to m-diisopropylbenzene dihydroperoxide with hydrogen peroxide and following said converting step, drying the product thereof prior to decomposing m-diisopropylbenzene dihydroperoxide so that the water content is not greater than about 0.1 wt %.

3. The process of claim 2 wherein said hydrogen peroxide is present in at least stoichiometric amounts.

4. The process of claim 2 wherein said hydrogen peroxide is present in excess amounts.

5. The process of claim 1 further comprising recycling about eighty percent of said oxidation products which remain following the extraction of said mixture, to a feed stream of said diisopropylbenzene for further oxidation.

6. The process of claim 1 wherein said organic solvent is methyl isobutyl ketone.

7. The process of claim 1 wherein said catalyst is boron trifluoride and said effective amount is in the range of about 10 to 100 ppm.

8. The process of claim 1 wherein said catalyst is boron trifluoride and said effective amount is in the range of about 10 to 50 ppm.

9. The process of claim 1 wherein said catalyst is neutralized following decomposition of m-diisopropylbenzene dihydroperoxide.

10. A process for the preparation of resorcinol comprising the steps of:
   oxidizing a feed stream of diisopropylbenzene under anhydrous, non-alkaline conditions with oxygen at a temperature of about 85° C.-95° C. wherein said diisopropylbenzene in said feed stream is comprised of major amounts of the m-isomer and less than about six percent of the o-isomer;
   extracting a mixture of m-diisopropylbenzene dihydroperoxide and m-diisopropylbenzene hydroxyhydroperoxide from products of said oxidizing step with dilute sodium hydroxide and recycling about eighty percent of the remaining said products to said feed stream;
   re-extracting said mixture from said sodium hydroxide with an organic solvent;
   treating said mixture with excess hydrogen peroxide to convert said mi-diisopropylbenzene hydroxyhydroperoxide to m-diisopropylbenzene dihydroperoxide;
   thereafter, drying the product of said treating step;
   decomposing m-diisopropylbenzene dihydroperoxide to produce a decomposition product containing resorcinol; and
   purifying said decomposition product to produce resorcinol.

11. The process of claim 10 wherein said decomposition of m-diisopropylbenzene dihydroperoxide is carried out in the presence of an effective amount of a catalyst selected from the group consisting of boron trifluoride, ferric chloride and stannic chloride and said step of drying said m-diisopropylbenzene dihydroperoxide prior to the decomposition thereof is sufficient to remove water so that the water content is no greater than about 0.1 wt %.

12. The process of claim 11 wherein said drying is achieved with a molecular sieve.

13. The process of claim 10 wherein said catalyst is neutralized following decomposition of m-diisopropylbenzene dihydroperoxide.

14. The process of claim 2 wherein said organic solvent is methyl isobutyl ketone and further comprising the steps of evaporating said methyl isobutyl ketone following said re-extraction step and dissolving said mixture in toluene prior to said conversion step.

15. The process of claim 10 wherein said organic solvent is methyl isobutyl ketone and further comprising the steps of evaporating said methyl isobutyl ketone following said re-extraction step and dissolving said mixture in toluene prior to said treating step.

* * * * *

UNITED STATES PATENT AND TRADEMARK OFFICE
CERTIFICATE OF CORRECTION

PATENT NO. : 4,849,549
DATED : July 18, 1989
INVENTOR(S) : CHING-YONG WU

It is certified that error appears in the above-identified patent and that said Letters Patent is hereby corrected as shown below:

In the Abstract, last line, "actone" should be --acetone--.

Col. 14, line 59, "o-dIPB" should be --o-DIPB--.

Col. 21, TABLE X, in the subheading above the last two columns, "w/o $H_2O_2$ Oxidn." should be --w/$H_2O_2$ Oxidn.--.

Col. 22, TABLE XI, in the subheading of the fourth column, "Solvent" should be --Solvent$^1$--.

Col. 23, line 18, "CLG" should be --GLC--.

Col. 23, line 30, "21.7%" should be --2.7%--.

Col. 24, line 49, "13.5 g" should be --1-3.5 g--.

Col. 25, TABLE XVI, under the "Type" column, the third entry "$FeCl_{13}$" should be --$FeCl_3$--.

Claim 1, col. 25, line 68, "amount" should be --amounts--.

Claim 10, col. 26, line 60, "mi-diisopropylbenzene" should be --m-diisopropylbenzene--.

UNITED STATES PATENT AND TRADEMARK OFFICE
CERTIFICATE OF CORRECTION

PATENT NO.  : 4,849,549

DATED       : July 18, 1989

INVENTOR(S) : CHING-YONG WU

It is certified that error appears in the above-identified patent and that said Letters Patent is hereby corrected as shown below:

Top of Columns 5 and 6, in the four groups of atom formulations, all four occurrences of the chemical symbol "OCH" should be --OOH--.

Col. 5, at approximately line 39, "OCH" should be --OOH--.

Col. 5, at approximately line 49, "OCH" (two occurrences) should be --OOH--.

Col. 5, at approximately line 56, "OCH" should be --OOH--.

Col. 6, at approximately line 33, "OCH" should be --OOH--.

Col. 11, line 60, "OCH" should be --OOH--.

Col. 12, at approximately line 13, "OCH" (two occurrences) should be --OOH--.

Col. 12, at approximately lines 20, 26 and 33, "OCH" should be --OOH--.

Col. 12, line 35, "OCH" (both occurrences) should be --OOH--.

Signed and Sealed this

Seventh Day of August, 1990

*Attest:*

HARRY F. MANBECK, JR.

*Attesting Officer*   *Commissioner of Patents and Trademarks*